US009867544B2

(12) United States Patent
Kim (10) Patent No.: US 9,867,544 B2
(45) Date of Patent: Jan. 16, 2018

(54) SPECTROMETER INCLUDING VERTICAL STACK STRUCTURE AND NON-INVASIVE BIOMETRIC SENSOR INCLUDING THE SPECTROMETER (71) Applicant: SAMSUNG ELECTRONICS CO., LTD., Suwon-si (KR)

(72) Inventor: Dongho Kim, Seoul (KR)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 135 days.

(21) Appl. No.: 14/821,933

(22) Filed: Aug. 10, 2015

(65) Prior Publication Data
US 2016/0120410 A1 May 5, 2016

(30) Foreign Application Priority Data
Nov. 3, 2014 (KR) .................. 10-2014-0151581

(51) Int. Cl.
A61B 5/00 (2006.01)
H01L 31/0304 (2006.01)
(Continued)

(52) U.S. Cl.
CPC .......... *A61B 5/0075* (2013.01); *G01J 3/0205* (2013.01); *G01J 3/0227* (2013.01); *G01J 3/0256* (2013.01);
(Continued)

(58) Field of Classification Search
CPC ........ A61B 5/0075; G01J 3/0227; G01J 3/32; G01J 3/42; G01J 3/44; G01J 3/4406; G01J 3/0259; G01J 3/0272
See application file for complete search history.

(56) References Cited

U.S. PATENT DOCUMENTS 5,272,340 A * 12/1993 Anbar .................. G01J 3/32
250/330
6,583,873 B1 * 6/2003 Goncharov ............. G01J 3/06
356/326
(Continued)

FOREIGN PATENT DOCUMENTS

EP 2746738 A2 6/2014
JP 2011185634 A 9/2011
(Continued)

OTHER PUBLICATIONS

Communication dated May 3, 2016, issued by the European Patent Office in counterpart European Application No. 15189017.5.

Primary Examiner — Dominic J Bologna
(74) Attorney, Agent, or Firm — Sughrue Mion, PLLC (57) ABSTRACT Provided are a spectrometer that may be easily manufactured while having high resolution and sensitivity due to reduced light loss and a non-invasive biometric sensor including the spectrometer. The spectrometer includes: a stacked light absorbing structure including a plurality of absorbing layers stacked in a vertical direction and having different absorption wavelength bands, and a plurality of tunnel junction layers respectively interposed between the plurality of absorbing layers to electrically connect the plurality of absorbing layers; and an illuminating unit configured to provide the stacked light absorbing structure with an illumination light for saturation of the plurality of absorbing layers.

23 Claims, 7 Drawing Sheets (51) Int. Cl.
*G01J 3/51* (2006.01)
*G01J 3/02* (2006.01)
*G01J 3/10* (2006.01)
*G01J 3/32* (2006.01)
*G01J 3/42* (2006.01)
*G01J 3/44* (2006.01)
*H01L 31/103* (2006.01)
*G01J 3/12* (2006.01)

(52) U.S. Cl.
CPC ........... *G01J 3/0259* (2013.01); *G01J 3/0272* (2013.01); *G01J 3/10* (2013.01); *G01J 3/32* (2013.01); *G01J 3/42* (2013.01); *G01J 3/44* (2013.01); *G01J 3/4406* (2013.01); *G01J 3/51* (2013.01); *H01L 31/1035* (2013.01); *G01J 2003/1213* (2013.01); *G01J 2003/1226* (2013.01)

(56) References Cited

U.S. PATENT DOCUMENTS

| | | | |
|---|---|---|---|
| 6,930,336 B1 | 8/2005 | Merrill | |
| 7,701,571 B2 | 4/2010 | Azimi et al. | |
| 8,350,208 B1 * | 1/2013 | Zhang | H01L 27/14647 250/214.1 |
| 8,461,567 B2 | 6/2013 | Voutilainen et al. | |
| 8,610,129 B2 | 12/2013 | Nam et al. | |
| 2005/0225630 A1 * | 10/2005 | Childers | H04N 13/0044 348/51 |
| 2010/0027001 A1 * | 2/2010 | Moser | G01J 3/02 356/301 |
| 2012/0129269 A1 | 5/2012 | Choi et al. | |
| 2013/0193308 A1 * | 8/2013 | Cellek | H01L 31/1013 250/208.1 |
| 2014/0170765 A1 * | 6/2014 | Ockenfuss | G01J 3/0256 436/501 |
| 2016/0305868 A1 | 10/2016 | Uematsu et al. | |

FOREIGN PATENT DOCUMENTS

| | | |
|---|---|---|
| JP | 2012242115 A | 12/2012 |
| JP | 2013228322 A | 11/2013 |
| KR | 10-2010-0022614 A | 3/2010 |
| KR | 10-1281169 B1 | 7/2013 |
| KR | 1020140001414 A | 1/2014 |
| KR | 10-2014-0044426 A | 4/2014 |
| KR | 101447113 B1 | 10/2014 |
| WO | 2005/099279 A1 | 10/2005 |

* cited by examiner

SPECTROMETER INCLUDING VERTICAL STACK STRUCTURE AND NON-INVASIVE BIOMETRIC SENSOR INCLUDING THE SPECTROMETER

CROSS-REFERENCE TO RELATED APPLICATION

This application claims priority from Korean Patent Application No. 10-2014-0151581, filed on Nov. 3, 2014 in the Korean Intellectual Property Office, the disclosure of which is incorporated herein in its entirety by reference.

BACKGROUND

1. Field

Apparatuses and methods consistent with exemplary embodiments relate to a spectrometer including a vertical stack structure and a non-invasive biometric sensor including the spectrometer, and more particularly, to a spectrometer that may be easily manufactured while having high resolution and sensitivity due to reduced light loss and a non-invasive biometric sensor including the spectrometer.

2. Description of the Related Art

A method considered to have the most potential as a method for non-invasive blood sugar measurement is a method of spectroscopic analysis of light including a biometric signal, which is scattered by a skin after being radiated to the skin. Recently, with improvements in performance of mobile apparatuses such as mobile phones, various attempts have been made to integrate a non-invasive biometric sensor into a mobile apparatus. To this end, it is necessary to develop a micro spectrometer that may be installed in a mobile apparatus.

For example, a linear variable filter (LVF)-based spectrometer has a structure in which a spacer having a gradually changing thickness is disposed on a plurality of photodiode pixels. Based on the principle that the transmission wavelength varies depending on the thickness of the spacer, lights of different wavelength bands may be sensed in the respective pixels. Also, a filter array-based spectrometer has a structure in which band-pass filters (BPFs) of different transmission bands are disposed in respective photodiode pixels.

The above spectrometers may be manufactured to be a micro sized. However, since a plurality of photodiode pixels are arranged in a horizontal direction, the resolution thereof is difficult to increase. Also, since the spacer or the BPFs absorb lights of wavelength bands other than the transmission bands, sensitivity degradation may occur due to light loss. For example, when N wavelength bands (where N is an integer equal to or greater than 1) are to be analyzed by the spectrometer, N different BPFs are used and the amount of light sensed by each pixel is only 1/N of the amount of light that is actually input to the pixel.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a spectrometer that may be easily manufactured while having high resolution and sensitivity due to reduced light loss and a non-invasive biometric sensor including the spectrometer.

According to an aspect of an exemplary embodiment, a spectrometer includes: a stacked light absorbing structure including a plurality of absorbing layers stacked in a vertical direction and having different absorption wavelength bands, and a plurality of tunnel junction layers respectively interposed between the plurality of absorbing layers to electrically connect the plurality of absorbing layers; and an illuminating unit configured to select an absorbing layer from among the plurality of absorbing layers, the selected absorbing layer being of one absorption wavelength band of the plurality of absorption wavelength bands, and provide the stacked light absorbing structure with an illumination light including other absorption wavelength bands of the plurality of absorption wavelength bands, of other absorbing layers of the plurality of absorbing layers.

For example, the illuminating unit may include: a light source configured to generate an illumination light including the absorption wavelength bands of the plurality of absorbing layers; and a notch filter array disposed between the light source and the stacked light absorbing structure and including a plurality of notch filters having different absorption characteristics to block only an illumination light of a wavelength band selected from among the absorption wavelength bands of the plurality of absorbing layers and transmit an illumination light of the other wavelength bands.

For example, each of the plurality of notch filters may have a sector shape, and the notch filter array may have a rotatable disk shape that is formed by connecting the plurality of notch filters on a rotation axis.

Each of the plurality of absorbing layers may include a positive-negative (p-n) junction.

Each of the plurality of tunnel junction layers may include a p-n junction that is doped at a higher doping concentration than the p-n junction of each of the plurality of absorbing layers.

The plurality of absorbing layers may be arranged in descending order of energy band gap from a light input side.

Each of the plurality of tunnel junction layers may have a larger energy band gap than the plurality of absorbing layers.

The plurality of absorbing layers and the plurality of tunnel junction layers may include a compound semiconductor.

For example, the plurality of absorbing layers and the plurality of tunnel junction layers may be formed of a material including any one selected from a combination including gallium arsenic phosphide (GaAsP), gallium arsenide (GaAs), and indium gallium arsenide (InGaAs), a combination including aluminum gallium arsenide (AlGaAs), GaAs, and InGaAs, a combination including InGaAs, GaAs, and gallium phosphide (GaP), and a combination including indium arsenide (InAs), GaAs, and gallium nitride (GaN).

For example, each of the plurality of absorbing layers may have a thickness of about 10 nm to about 10 μm.

Each of the plurality of tunnel junction layers may have a thickness of, for example, about 10 nm to about 100 nm.

The spectrometer may further include: a first electrode disposed on a bottom surface of the stacked light absorbing structure; and a second electrode disposed on a top surface of the stacked light absorbing structure, wherein the plurality of absorbing layers may be electrically connected in series between the first electrode and the second electrode.

The first electrode may be disposed on a bottom surface of an absorbing layer having the smallest energy band gap among the plurality of absorbing layers, and the second electrode may be disposed on a top surface of an absorbing layer having the largest energy band gap among the plurality of absorbing layers.

The spectrometer may further include a controller configured to control the illuminating unit to change the absorption wavelength bands included in the illumination light by changing the selected absorbing layer with the lapse of time, and measure a photocurrent generated by the stacked light absorbing structure when the selected absorbing layer is changed.

The controller may be configured to store a pre-measured external quantum efficiency or short-circuit current density of each of the plurality of absorbing layers.

According to another aspect of an exemplary embodiment, a non-invasive biometric sensor includes: a light source unit configured to irradiate an excitation light to an object; a spectrometer configured to measure a spectrum distribution of a scattered light generated from the object by the excitation light; and a controller configured to control operations of the spectrometer and analyze properties of the object by using signals provided by the spectrometer, the spectrometer including: a stacked light absorbing structure including a plurality of absorbing layers stacked in a vertical direction and having different absorption wavelength bands, and a plurality of tunnel junction layers respectively interposed between the plurality of absorbing layers to electrically connect the plurality of absorbing layers; and an illuminating unit configured to select an absorbing layer from among the plurality of absorbing layers and provide the stacked light absorbing structure with an illumination light including the absorption wavelength bands of the other absorbing layers, other than the absorption wavelength band of the selected absorbing layer.

The scattered light and the illumination light may be together input to a light input surface of the stacked light absorbing structure, and the notch filter array may be disposed only on a path of the illumination light.

The controller may be configured to control the illuminating unit to change the absorption wavelength bands included in the illumination light by changing the selected absorbing layer with the lapse of time, and measure a photocurrent generated by the stacked light absorbing structure whenever the selected absorbing layer is changed.

The controller may be configured to calculate the spectrum distribution of the scattered light by using the pre-measured external quantum efficiency or short-circuit current density of each of the plurality of absorbing layers and photocurrent measurement values of the stacked light absorbing structure that are obtained whenever the selected absorbing layer is changed.

The non-invasive biometric sensor may further include a signal processor configured to analyze the properties of the object on the basis of the spectrum distribution of the scattered light.

The signal processor may analyze the physical properties of the object by Raman spectroscopy.

The non-invasive biometric sensor may further include a display unit configured to display the analysis results of the signal processor.

According to an aspect of another exemplary embodiment, a non-invasive biometric sensing method includes: radiating an excitation light to an object; providing a scattered light, which is generated from the object by the excitation light, to a stacked light absorbing structure, the stacked light absorbing structure including first to Nth absorbing layers stacked in a vertical direction and having different first to Nth absorption wavelength bands, and a plurality of tunnel junction layers respectively interposed between the first to Nth absorbing layers to electrically connect the first to Nth absorbing layers; providing the stacked light absorbing structure with an illumination light for saturation of the second to Nth absorbing layers, other than the first absorbing layer, together with the providing of the scattered light; measuring a first photocurrent generated by the stacked light absorbing structure; and calculating a light amount of a first wavelength band component in the scattered light by using the measured first photocurrent.

The non-invasive biometric sensing method may further include, after the calculating of the light amount of the first wavelength band component in the scattered light: providing the stacked light absorbing structure with an illumination light for saturation of the first and third to Nth absorbing layers, other than the second absorbing layer, together with the providing of the scattered light; measuring a second photocurrent generated by the stacked light absorbing structure; and calculating a light amount of a second wavelength band component in the scattered light by using the measured second photocurrent.

The non-invasive biometric sensing method may further include, after the calculating of the light amount of the second wavelength band component in the scattered light: providing the stacked light absorbing structure with the illumination light together with the scattered light; and repeating a photocurrent measuring operation to calculate light amounts of third to Nth wavelength band components in the scattered light.

For example, the calculating of the light amount of the first wavelength band component in the scattered light by using the measured first photocurrent may include calculating the light amount of the first wavelength band component in the scattered light by comparing the measured first photocurrent with a pre-measured short-circuit current density of the first absorbing layer.

According to another aspect of an exemplary embodiment, there is provided a biological signal sensor including: a stacked light absorbing structure comprising a plurality of light absorption layers configured to receive a light that saturates the plurality of light absorption layers excluding one of the plurality of light absorption layers and receive a bio-optical signal that activates the excluded light absorption layer, each of the plurality of light absorption layers being configured to absorb a different wavelength band of an optical spectrum; and a controller configured to measure a photocurrent generated from the stacked light absorbing structure and analyze the bio-optical signal based on the measured photocurrent.

The biological signal sensor may further include a memory configured to store a pre-measured short-circuit current density of the excluded light absorption layer, wherein the controller is further configured to compare the measured photocurrent to the pre-measured short-circuit current density to analyze the bio-optical signal.

The biological signal sensor may further include: a light source configured to radiate a light towards a top surface of the stacked light absorbing structure; and a notch filter configured to block, from the radiated light, a wavelength band that the excluded light absorption layer is capable of absorbing.

The biological signal sensor may further include: another light source configured to radiate a light towards a target subject to be reflected therefrom, wherein the reflected light carries the bio-optical signal.

BRIEF DESCRIPTION OF THE DRAWINGS

The above and/or other aspects will be more apparent by describing certain exemplary embodiments, with reference to the accompanying drawings, in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

Hereinafter, a spectrometer including a vertical stack structure and a non-invasive biometric sensor including the spectrometer will be described in detail with reference to the accompanying drawings. In the drawings, like reference numerals denote like elements, and the sizes of components may be exaggerated for clarity. The embodiments described hereinafter are merely exemplary, and various changes and modifications may be made therein. It will be understood that when a layer is referred to as being "on" another layer, it may be directly on the other layer, or one or more intervening layers may also be present.

Figure 1:
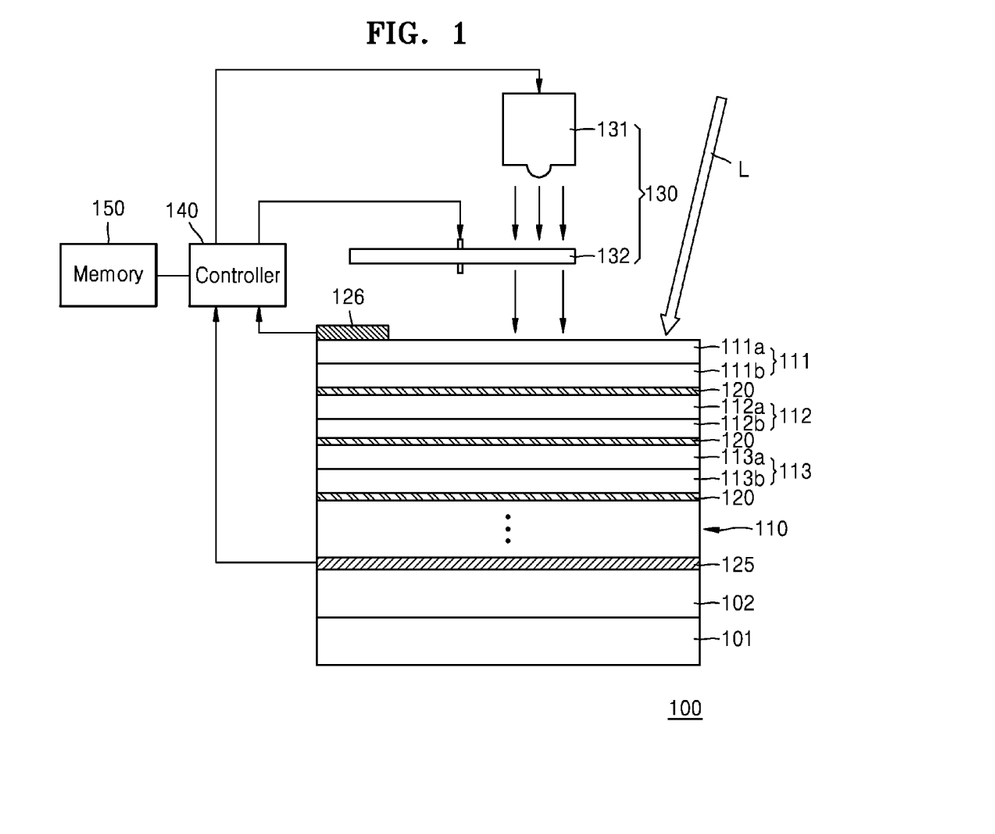
FIG. 1 is a schematic diagram illustrating a structure of a spectrometer according to an exemplary embodiment.

FIG. 1 is a schematic diagram illustrating a structure of a spectrometer 100 according to an exemplary embodiment. Referring to FIG. 1, the spectrometer 100 according to the present exemplary embodiment may include a stacked light absorbing structure 110 configured to generate a photocurrent by absorbing lights of a plurality of different wavelength bands, and an illuminating unit 130 configured to selectively provide a light of a predetermined wavelength band to the stacked light absorbing structure 110. Also, the spectrometer 100 may further include a controller 140 configured to control the illuminating unit 130 to select the wavelength band of the light provided to the stacked light absorbing structure 110, and measure the photocurrent generated by the stacked light absorbing structure 110.

The stacked light absorbing structure 110 may include a plurality of absorbing layers 111, 112, and 113 stacked in a vertical direction and having different absorption wavelength bands, and a plurality of tunnel junction layers 120 respectively interposed between the plurality of absorbing layers 111, 112, and 113 to electrically connect the plurality of absorbing layers 111, 112, and 113. The stacked light absorbing structure 110 may be formed on a substrate 101 formed of, for example, silicon (Si), gallium nitride (GaN), gallium phosphide (GaP), or the like. Also, according to an exemplary embodiment, a buffer layer 102 may be first formed on the substrate 101, and then the stacked light absorbing structure 110 may be formed on the buffer layer 102. The substrate 101 and the buffer layer 102 may be removed after formation of the stacked light absorbing structure 110.

Each of the absorbing layers 111, 112, and 113 may include a p-n junction structure configured to absorb a light of a predetermined wavelength band. For example, the first absorbing layer 111 may include an n-type doped layer 111a and a p-type doped layer 111b that have an energy band gap for absorbing a light of a first wavelength band. Also, the second absorbing layer 112 may include an n-type doped layer 112a and a p-type doped layer 112b that have an energy band gap for absorbing a light of a second wavelength band, and the third absorbing layer 113 may include an n-type doped layer 113a and a p-type doped layer 113b that have an energy band gap for absorbing a light of a third wavelength band. Each of the absorbing layers 111, 112, and 113 may be excited by a light corresponding to its absorption wavelength band to generate a photocurrent proportional to the intensity of light.

According to the present exemplary embodiment, the absorbing layers 111, 112, and 113 may be arranged in descending order of energy band gap from a light input side. Thus, the energy band gaps of the absorbing layers 111, 112, and 113 may decrease gradually along a light propagation direction. For example, the first absorbing layer 111 disposed at the top of the stacked light absorbing structure 110 may have the largest energy band gap, the second absorbing layer 112 disposed under the first absorbing layer 111 may have a smaller energy band gap than the first absorbing layer 111, and the third absorbing layer 113 disposed under the second absorbing layer 112 may have a smaller energy band gap than the second absorbing layer 112. Then, the first absorbing layer 111 may be excited by a light of the shortest wavelength band among the plurality of absorbing layers 111, 112, and 113, and the second absorbing layer 112 may be excited by a light of a longer wavelength band than the first absorbing layer 111. That is, when the energy band gaps of the first to third absorbing layers 111, 112, and 113 are respectively Eg1, Eg2, and Eg3 from the light input side, a relationship of Eg1>Eg2>Eg3 may be satisfied. Also, when the absorption wavelengths of the first to third absorbing layers 111, 112, and 113 are respectively $\lambda 1$, $\lambda 2$, and $\lambda 3$, a relationship of $\lambda 1 < \lambda 2 < \lambda 3$ may be satisfied.

Also, since each of the absorbing layers 111, 112, and 113 absorbs a light corresponding to its absorption wavelength band, the upper absorbing layers 111 and 112 may function as filters for the lower absorbing layers 112 and 113 respectively. For example, since the first absorbing layer 111 absorbs a light of the first wavelength band, lights of wavelength bands other than the first wavelength band among the lights input to the stacked light absorbing structure 110 may be input to the second absorbing layer 112. Lights of wavelength bands other than the first and second wavelength bands among the lights input to the stacked light absorbing structure 110 may be input to the third absorbing layer 113.

The absorbing layers 111, 112, and 113 may include a compound semiconductor. For example, by using group III-V compound semiconductors suitable for band-gap engineering, the absorbing layers 111, 112, and 113 may be formed to have respective energy band gaps. For example, the absorbing layers 111, 112, and 113 may include $Al_XIn_{1-X}P$ (0<X<1), $In_XGa_{1-X}P_YAs_{1-Y}$ (0<X<1, 0<Y<1), $Al_XGa_{1-X}In_YP$ (0<X<1, 0<Y<1), or any combination thereof. As another example, depending on the wavelength bands for spectroscopy, the absorbing layers 111, 112, and 113 may be formed of a material including any one selected from a combination including gallium arsenic phosphide (GaAsP), gallium arsenide (GaAs), and indium gallium arsenide (InGaAs), a combination including aluminum gallium arsenide (AlGaAs), GaAs, and InGaAs, a combination including InGaAs, GaAs, and gallium phosphide (GaP), and a combination including indium arsenide (InAs), GaAs, and gallium nitride (GaN).

For example, when the spectrometer 100 according to the present exemplary embodiment is configured to spectroscope a light of a wavelength band of about 1.38 eV (about 900 nm) to about 1.55 eV (about 800 nm), the absorbing layers 111, 112, and 113 may include a combination including GaAsP, GaAs, and InGaAs or a combination including AlGaAs, GaAs, and InGaAs. Also, when the spectrometer 100 according to the present exemplary embodiment is configured to spectroscope a light of a wavelength band of about 0.62 eV (about 2 μm) to about 2.07 eV (about 600 nm), the absorbing layers 111, 112, and 113 may include a combination including InGaAs, GaAs, and GaP. Also, when the spectrometer 100 according to the present exemplary embodiment is configured to spectroscope a light of a wavelength band of about 0.41 eV (about 3 μm) to about 3.1 eV (about 400 nm), the absorbing layers 111, 112, and 113 may include a combination including InAs, GaAs, and GaN.

Although FIG. 1 illustrates only three absorbing layers 111, 112, and 113 for convenience sake, the stacked light absorbing structure 110 may include four or more absorbing layers in order to provide a high resolution. For example, the stacked light absorbing structure 110 may include eleven or more absorbing layers in order to analyze desired biometric information on the basis of biometric optical signals that are transmitted or scattered from a living body.

The thickness of each of the absorbing layers 111, 112, and 113 may vary depending on the material of each of the absorbing layers 111, 112, and 113. As described above, since each of the absorbing layers 111, 112, 113 functions as a filter for the lower absorbing layers, each of the absorbing layers 111, 112, and 113 may be formed to a thickness for sufficient light absorption. For example, each of the absorbing layers 111, 112, and 113 may have a thickness of about 10 nm to about 10 μm.

The tunnel junction layers 120 may be respectively disposed between the absorbing layers 111, 112, and 113 to electrically connect the absorbing layers 111, 112, and 113. The tunnel junction layers 120 may include the same compound semiconductor material as the absorbing layers 111, 112, and 113, but may be different from the absorbing layers 111, 112, and 113 in terms of doping concentration, energy band gap, and thickness. That is, the tunnel junction layers 120 may be doped at a high concentration in order to electrically connect the absorbing layers 111, 112, and 113. For example, the tunnel junction layers 120 may include a p-n junction that is doped at a higher doping concentration of about $10^{20}/cm^3$ than the p-n junctions of the absorbing layers 111, 112, and 113. Also, each of the tunnel junction layers 120 may have a thickness of about 10 nm to about 100 nm for tunneling effects. Also, the tunnel junction layers 120 may have a larger energy band gap than the absorbing layers 111, 112, and 113 in order to prevent the recombination of holes and electrons separated in each of the absorbing layers 111, 112, and 113.

According to the present exemplary embodiment, since the absorbing layers 111, 112, and 113 are connected in series by the tunnel junction layers 120, an electrode may not be connected to each of the absorbing layers 111, 112, and 113. As illustrated in FIG. 1, the spectrometer 100 according to the present exemplary embodiment may include a first electrode 125 disposed on a bottom surface of the stacked light absorbing structure 110, and a second electrode 126 disposed on a top surface of the stacked light absorbing structure 110. In other words, the first electrode 125 may be disposed on a bottom surface of the absorbing layer having the smallest energy band gap among the absorbing layers 111, 112, and 113, and the second electrode 126 may be disposed on a top surface of the absorbing layer having the largest energy band gap. The absorbing layers 111, 112, and 113 may be electrically connected in series between the first electrode 125 and the second electrode 126 by the tunnel junction layers 120 respectively disposed between the absorbing layers 111, 112, and 113.

The illuminating unit 130 provides the stacked light absorbing structure 110 with an illumination light for saturation of the absorbing layers 111, 112, and 113. In detail, under the control of the controller 140, the illuminating unit 130 may selectively provide a light of a predetermined wavelength band to the stacked light absorbing structure 110. For example, the illuminating unit 130 may select an absorbing layer from among the absorbing layers 111, 112, and 113 and provide the stacked light absorbing structure 110 with an illumination light including the absorption wavelength bands of the other absorbing layers, but not including the absorption wavelength band of the selected absorbing layer, through an operation of the illuminating unit 130 as described below.

To this end, the illuminating unit 130 may include a light source 131 configured to generate an illumination light including the absorption wavelength bands of the absorbing layers 111, 112, and 113, and a notch filter array 132 including a plurality of notch filters having different absorption characteristics. For example, the light source 131 may be a white light source providing a white light. Also, the light source 131 may provide not only a visible light but also an ultraviolet light or an infrared light. As another example, the light source 131 may include an array of a plurality of light-emitting diodes (LEDs) that emit lights corresponding to the absorption wavelength bands of the absorbing layers 111, 112, and 113, respectively. The light source 131 may be disposed to face a light input surface of the stacked light absorbing structure 110.

Figure 2:
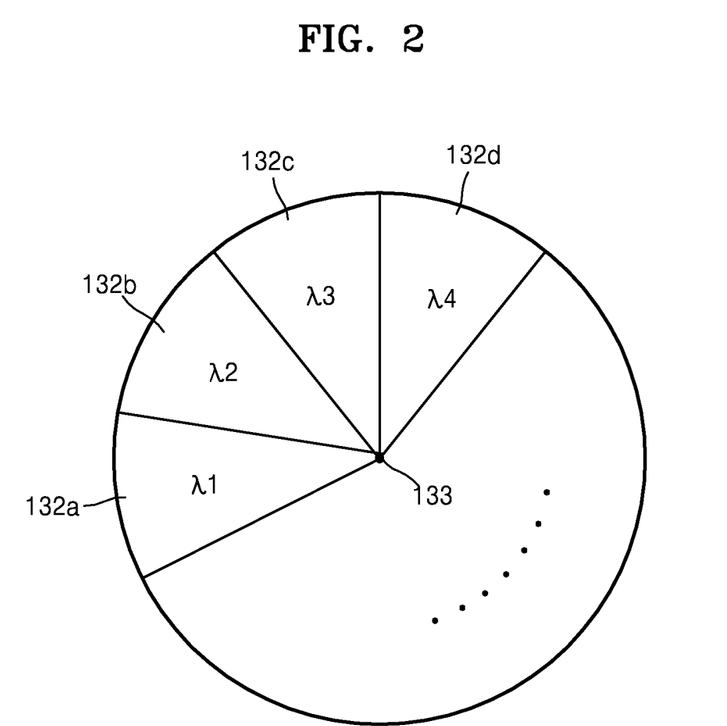
FIG. 2 is a plan view illustrating a configuration of a notch filter array.

The notch filter array 132 may be disposed between the light source 131 and the stacked light absorbing structure 110. Each of the notch filters of the notch filter array 132 may absorb only an illumination light of a wavelength band selected from among the absorption wavelength bands of the absorbing layers 111, 112, and 113 and transmit an illumination light of the other wavelength bands. For example, FIG. 2 is a plan view illustrating a configuration of the notch filter array 132. As illustrated in FIG. 2, each of notch filters 132a, 132b, 132c, and 132d may have a sector or a pie shape, and the notch filter array 132 may have a rotatable disk shape that is formed by connecting the notch filters 132a, 132b, 132c, and 132d on a common rotation axis 133. Herein, for example, the first notch filter 132a may absorb a light of the first wavelength band among the illumination lights and transmit lights of the other wavelength bands. Also, the second notch filter 132b may absorb a light of the second wavelength band among the illumination lights and transmit lights of the other wavelength bands. For example, the absorption wavelength band of the first notch filter 132a may be identical to the absorption wavelength band of the first absorbing layer 111, and the absorption wavelength band of the second notch filter 132b may be identical to the absorption wavelength band of the second absorbing layer 112.

The notch filter array 132 may rotate on the rotation axis 133 under the control of the controller 140. Then, any one selected from the notch filters 132a, 132b, 132c, and 132d may be located on a propagation path of the illumination light between the light source 131 and the stacked light absorbing structure 110. In this way, illumination lights having different spectrum distributions may be provided to the stacked light absorbing structure 110. For example, under the control of the controller 140, illumination lights of wavelength bands other than the light of the first wavelength band or illumination lights of wavelength bands other than the light of the second wavelength band may be provided to the stacked light absorbing structure 110.

However, when the light source 131 includes an array of a plurality of LEDs emitting lights of different wavelengths, the notch filter array 132 may not be used. For example, the light source 131 may include first to Nth LEDs emitting lights of first to Nth (herein, N is a natural number greater than 1) wavelength bands respectively. In this case, one selected LED may be turned off and the other LEDs may be turned on. For example, the LEDs other than the first LED or the LEDs other than the second LED may be turned on under the control of the controller 140.

Operations of the spectrometer 100 having the above structure will be described below.

As described above, according to the present exemplary embodiment, since the absorbing layers 111, 112, and 113 are electrically connected in series between the first electrode 125 and the second electrode 126, photocurrents generated respectively by the absorbing layers 111, 112, and 113 are sequentially measured with the lapse of time. To this end, an short-circuit current density and external quantum efficiency (EQE) of each of the absorbing layers 111, 112, and 113 may be measured and stored in advance. For example, the controller 140 may store a pre-measured short-circuit current density and EQE of each of the absorbing layers 111, 112, and 113.

Figure 3:
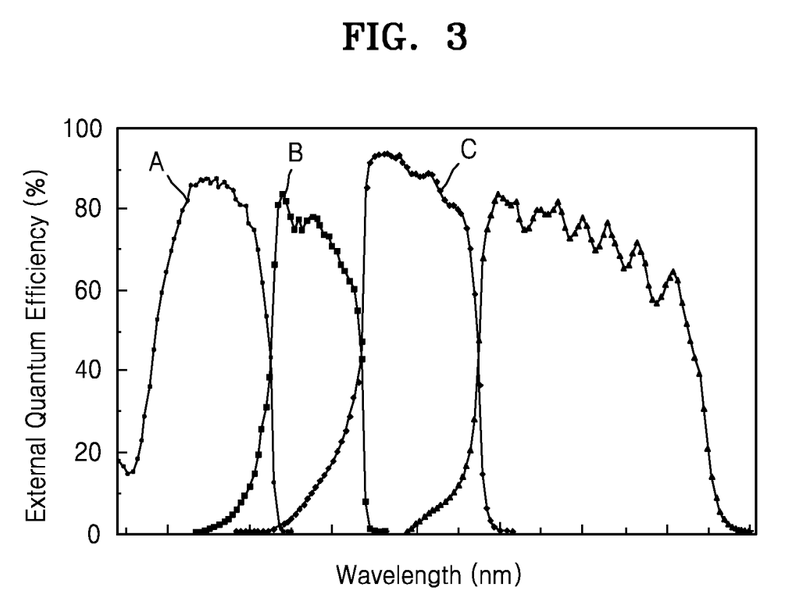
FIG. 3 is a graph illustrating the external quantum efficiency of an absorbing layer.
Figure 4:
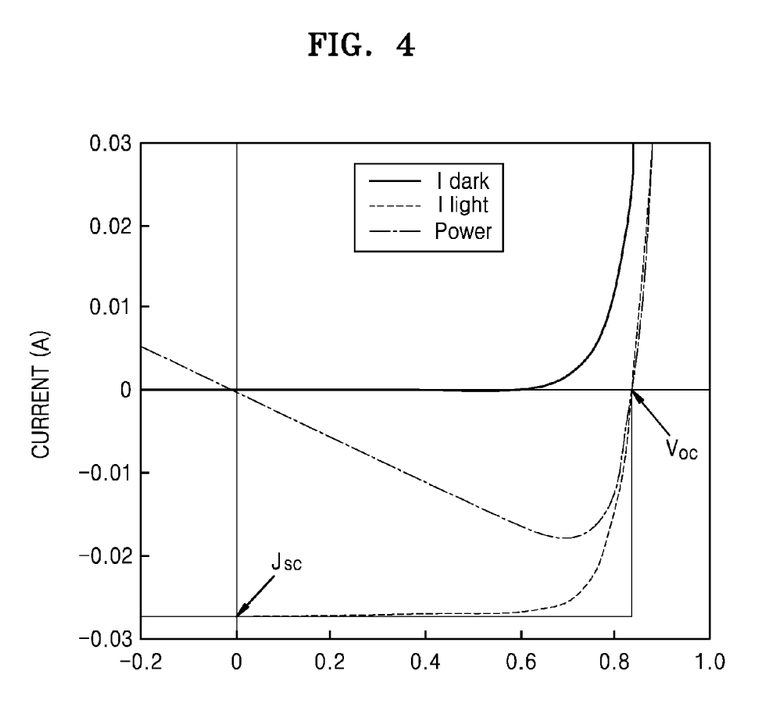
FIG. 4 is a graph illustrating a current-voltage characteristic change caused by light in an absorbing layer.

The short-circuit current density and the EQE may have unique values depending on the properties of materials of the absorbing layers 111, 112, and 113. For example, FIG. 3 is a graph illustrating the external quantum efficiency of the absorbing layers 111, 112, and 113, and FIG. 4 is a graph illustrating a current-voltage characteristic change caused by light in the absorbing layers 111, 112, and 113. In FIG. 3, a curve A may represent an example of the EQE of the first absorbing layer 111, a curve B may represent an example of the EQE of the second absorbing layer 112, and a curve C may represent an example of the EQE of the third absorbing layer 113. Also, in FIG. 4, a solid-line curve may be an example of a current-voltage curve when a light is not input, and a dotted-line curve may be an example of a current-voltage curve when a light is input. The short-circuit current density is a current in the case where both ends of each of the absorbing layers 111, 112, and 113 are short-circuited, that is, in the case where a voltage between both ends of each of the absorbing layers 111, 112, and 113 is 0 V. In FIG. 4, Voc denotes an open-circuit voltage in the case where a current is 0 A.

The spectrometer 100 may further include a memory 150 that stores information of the current-voltage curve and/or characteristics which are measured with respect to each of the absorbing layers 111, 112, and 113 when the light is turned on and off respectively. In addition, the memory 150 may store voltage-power characteristics of each of the absorbing layers 111, 112, and 113. The power may refer to a total radiant flux (mW) of the light source 131. Further, the memory 150 may include the EQEs of the first, second and third absorbing layers 111, 112, and 113. Although FIG. 1 illustrates the memory 150 separately from the controller 140, the memory 150 may be embedded in the controller 140.

The short-circuit current density and the EQE of each of the absorbing layers 111, 112, and 113 may be obtained by sequentially inputting lights of different wavelength bands to the stacked light absorbing structure 110 illustrated in FIG. 1. For example, the saturated short-circuit current density and the EQE of the first absorbing layer 111 may be obtained by providing the stacked light absorbing structure 110 with a light of the first wavelength band having a light amount for saturation of the first absorbing layer 111 and then measuring a current flowing between the first electrode 125 and the second electrode 126. Thereafter, the saturated short-circuit current density and the EQE of the second absorbing layer 112 may be obtained by providing the stacked light absorbing structure 112 with a light of the second wavelength band having a light amount for saturation of the second absorbing layer 112 and then measuring a current flowing between the first electrode 125 and the second electrode 126. In this way, the saturated short-circuit current densities and the EQEs of all the absorbing layers may be obtained by sequentially inputting lights of different wavelength bands. As another example, data about a change in the short-circuit current density caused by a change in the intensity of light may be obtained by changing the intensity of a light of each wavelength band.

In actual spectroscopic analysis, an illumination light input directly from the illuminating unit 130 and a scattered light generated by an object may be together input to the stacked light absorbing structure 110. The scattered light may be generated when an radiated excitation light is reflected by the object or penetrates the object. For example, the illumination light and the excitation light may be generated by separate light sources. However, as another example, a light emitted from one light source may be split by a beam splitter or the like, a portion of the split light may be provided to the notch filter array 132, and the other portion of the split light may be radiated as the excitation light to the object. The saturated short-circuit current densities and the EQEs of the first, second, and third absorbing layers 111, 112, and 113 may be stored in the memory 150.

In this case, under the control of the controller 140, the illuminating unit 130 may select an absorbing layer from among the absorbing layers 111, 112, and 113 and provide the stacked light absorbing structure 110 with an illumination light including the absorption wavelength bands of the other absorbing layers, other than the absorption wavelength band of the selected absorbing layer. The controller 140 may control the illuminating unit 130 to change the absorption wavelength bands included in the illumination light by changing the selected absorbing layer with the lapse of time. Also, the controller 140 may measure a photocurrent generated by the stacked light absorbing structure 110 whenever the selected absorbing layer is changed, and calculate the intensity of a light of the wavelength band absorbed by the selected absorbing layer by using the measured photocurrent. For example, the controller 140 may calculate the amount of the light of the wavelength band absorbed by the selected absorbing layer by comparing the measured photocurrent with the pre-measured short-circuit current density of the selected absorbing layer. As another example, based on the relationship of (Number of Photons)×EQE=(Number of Electrons), the controller 140 may calculate the amount of the light of the wavelength band absorbed by the selected absorbing layer by using the measured photocurrent and the pre-measured EQE of the selected absorbing layer.

In detail, referring to FIG. 1, an excitation light is radiated to an object, and a scattered light L generated from the object by the excitation light is provided to the stacked light absorbing structure 110. At the same time, the illuminating unit 130 may provide the stacked light absorbing structure 110 with an illumination light for saturation of the second and third absorbing layers 112 and 113 other than the first absorbing layer 111. For example, the controller 140 may rotate the notch filter array 132 to locate the first notch filter 132a of the notch filter array 132 on a path of the illumination light. Then, illumination lights having wavelength bands other than the first wavelength band may be input to the stacked light absorbing structure 110. Accordingly, the second and third absorbing layers 112 and 113 may be in a saturated state.

Since a light of the first wavelength band is not included in the illumination light, the light of the first wavelength band absorbed by the first absorbing layer 111 is provided from the scattered light L. Since the intensity of the scattered light L is much smaller than the intensity of the illumination light, the photocurrent generated by the first absorbing layer 111 may be smaller than the photocurrents generated by the saturated second and third absorbing layers 112 and 113. Also, since the absorbing layers 111, 112, and 113 are connected in series, the current flowing between the first electrode 125 and the second electrode 126 of the stacked light absorbing structure 110 may be limited to the smallest photocurrent among the photocurrents generated by the absorbing layers 111, 112, and 113.

According to another exemplary embodiment, the notch filter 132 may be omitted from the spectrometer 100. In that case, the light source 131 itself may be capable of radiating a light only in the first and the second wavelength bands, a light only in the first and third wavelengths bands, and a light only in the second and third wavelengths bands, under the control of the controller 140. For example, the controller 140 may control the light source 131 to radiate a light only in the first and third wavelength bands so that the first and the third absorbing layers 111 and 113 are saturated. Thereby, the spectrometer 100 may detect the second wavelength band of a bio-optical signal, which is reflected and/or refracted from a target subject (e.g., human subject), when the unsaturated second absorbing layer 112 is activated by the second wavelength band of the bio-optical signal.

Figure 5:
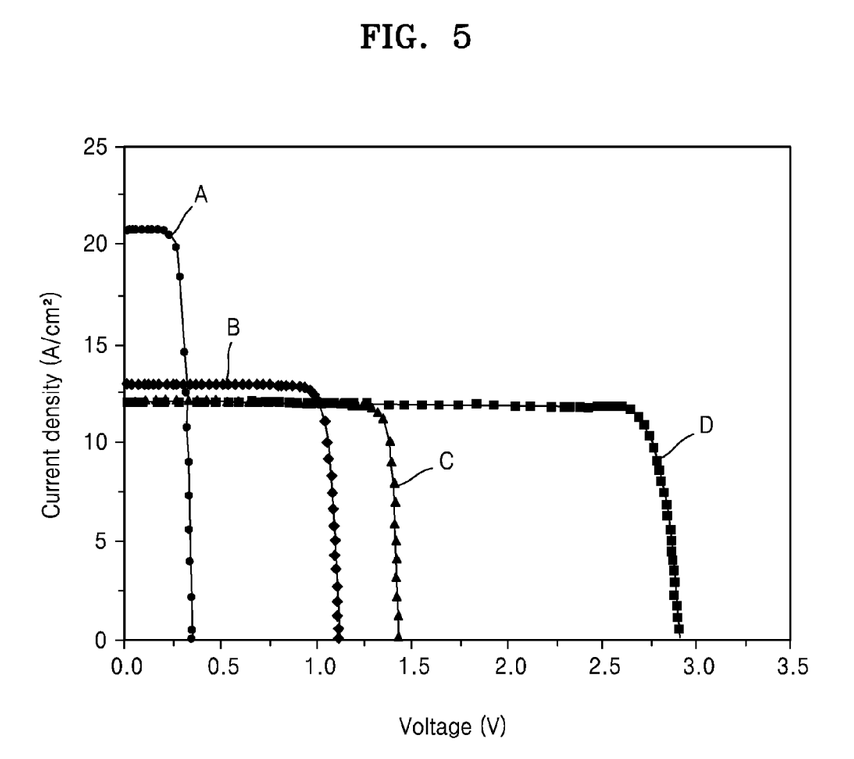
FIG. 5 is a graph illustrating the overall current-voltage characteristics of a stacked light absorbing structure and an absorbing layer.

For example, FIG. 5 is a graph illustrating the overall current-voltage characteristics of the stacked light absorbing structure 110 and the absorbing layers 111, 112, and 113. In FIG. 5, a curve A may represent an example of the current-voltage characteristics of the first absorbing layer 111, a curve B may represent an example of the current-voltage characteristics of the second absorbing layer 112, a curve C may represent an example of the current-voltage characteristics of the third absorbing layer 113, and a curve D may represent an example of the overall current-voltage characteristics of the stacked light absorbing structure 110. As may be seen from FIG. 5, the short-circuit current density of the stacked light absorbing structure 110 may be equal to the lowest short-circuit current density among the short-circuit current densities of the first to third absorbing layers 111, 112, and 113, and the open-circuit voltage of the stacked light absorbing structure 110 may be equal to the sum of the open-circuit voltages of the first to third absorbing layers 111, 112, and 113.

Thus, when the second and third absorbing layers 112 and 113 are saturated, the photocurrent generated by the first absorbing layer 111 may be measured by measuring the current flowing between the first electrode 125 and the second electrode 126 of the stacked light absorbing structure 110. Then, the intensity of the light of the first wavelength band absorbed by the first absorbing layer 111 may be calculated by using the measured photocurrent. For example, the amount of the light of the first wavelength band absorbed by the first absorbing layer 111 may be calculated by comparing the measured photocurrent with the pre-measured short-circuit current density of the first absorbing layer 111. As another example, the amount of the light of the first wavelength band absorbed by the first absorbing layer 111 may be calculated by using the measured photocurrent and the pre-measured EQE of the first absorbing layer 111. In this way, the amount of the light of the first wavelength band included in the scattered light L may be detected.

Thereafter, the controller 140 may rotate the notch filter array 132 to locate the second notch filter 132b of the notch filter array 132 on the path of the illumination light. Then, illumination lights having wavelength bands other than the second wavelength band may be input to the stacked light absorbing structure 110. Accordingly, the first and third absorbing layers 111 and 113 may be in a saturated state. Thus, since the current flowing between the first electrode 125 and the second electrode 126 of the stacked light absorbing structure 110 is equal to the photocurrent generated by the second absorbing layer 112, the amount of the light of the second wavelength band included in the scattered light L may be detected by measuring the generated photocurrent. When the above method is repeated for all the wavelength bands on the basis of this principle, the spectrum distribution of the scattered light L in all the relevant wavelength bands may be analyzed.

According to the present exemplary embodiment, since the absorbing layers 111, 112, and 113 are arranged in the vertical direction, the occupation area of the spectrometer 100 may be greatly reduced and the resolution of the spectrometer 100 may be improved. Also, since there is little light loss, the sensitivity of the spectrometer 100 may be improved. Thus, since the spectrometer 100 according to the present exemplary embodiment 100 may be manufactured in a micro size, a non-invasive biometric sensor installed in a mobile apparatus may be implemented.

Figure 6:
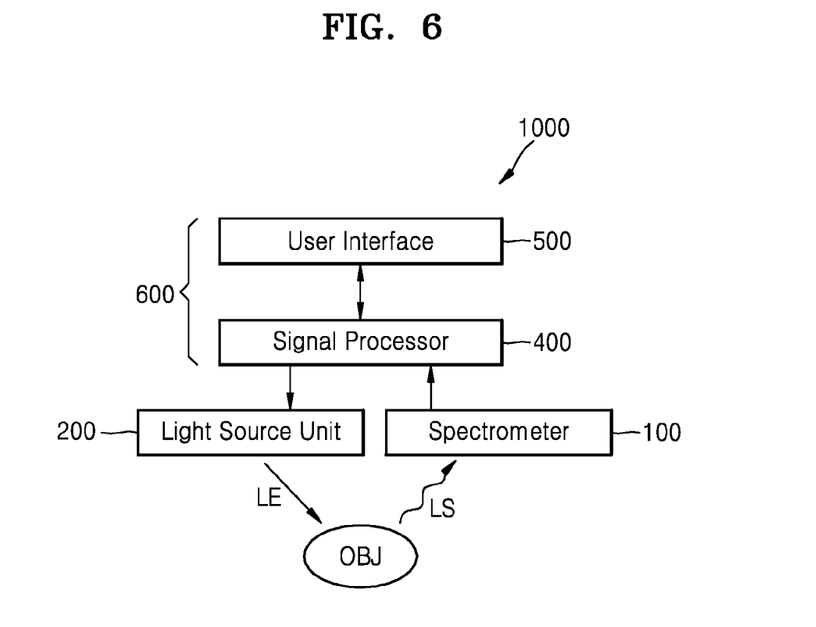
FIG. 6 is a block diagram illustrating a structure of a non-invasive biometric sensor including the spectrometer of FIG. 1 according to an exemplary embodiment.

For example, FIG. 6 is a block diagram illustrating a structure of a non-invasive biometric sensor 1000 including the spectrometer 100 of FIG. 1 according to an exemplary embodiment. Referring to FIG. 6, the non-invasive biometric sensor 1000 may include a light source unit 200 configured to radiate an excitation light LE to an object OBJ, and a spectrometer 100 configured to spectroscope a scattered light LS generated from the object OBJ. Herein, the object OBJ may include a human body, a living body of an animal, or a food. For example, the object OBJ may be a human body for blood sugar measurement or a food for freshness measurement, and may be a sample for analysis of air pollution or water pollution.

The light source unit 200 may include a light source and may also include at least one optical member for guiding the light from the light source to a desired position of the object OBJ. The light source may be configured to radiate a light of a wavelength band suitable for an analysis target property of the object OBJ. For example, the light source may radiate a near-infrared light of a wavelength band of about 0.8 µm to about 2.5 µm. The light source may include, for example, an LED or a laser diode (LD). As described above, the light source of the light source unit 200 may be separate from the light source 131 of the illuminating unit 130 of the spectrometer 100.

Referring back to FIG. 6, the non-invasive biometric sensor 1000 may further include a controller 600 configured to analyze the properties of the object OBJ on the basis of signals sensed by the spectrometer 100 and generate necessary control signals. The controller 600 may include a user interface 500 and a signal processor 400. The user interface 500 may include an input unit and a display. The signal processor 400 may analyze the properties of the object OBJ on the basis of the signals sensed by the spectrometer 100. For example, the signal processor 400 may analyze the properties of the object OBJ by Raman spectroscopy or near-infrared (NIR) absorption spectrum analysis. The Raman spectroscopy may use scattering (particularly inelastic scattering) in which the light input into the object OBJ is scattered in various directions by colliding with molecules or atoms included in the object OBJ. In the inelastic scattering, instead of being simply reflected from the surface of molecules or atoms, the input light is emitted after being absorbed into molecules or atoms, wherein the scattered light may have a longer wavelength than the input light and a wavelength difference between the scattered light and the input light may be about 200 nm or less. Various properties, such as the structure of molecules and the vibration of molecules in the object OBJ, may be detected by analyzing the spectrum of the scattered light.

The signal processor 400 may process the analysis result into a video signal to be displayed on the display unit of the user interface 500. Also, the signal processor 400 may transmit a control signal to the light source unit 200 according to the input from the user interface 500. For example, the signal processor 400 may be implemented by a microprocessor.

The spectrometer 100 and the controller 600 may be connected to each other by wire or wirelessly. For example, the non-invasive biometric sensor 1000 may be implemented as a mini portable device in which the spectrometer 100 and the controller 600 are connected by wire. As another example, the controller 600 may be mounted on a portable mobile communication device to wirelessly communicate with the spectrometer 100. The controller 140 of the spectrometer 100 illustrated in FIG. 1 may be a portion of the controller 600 of the non-invasive biometric sensor 100 illustrated in FIG. 6 or may be integrated with the controller 600. For example, the controller 140 of the spectrometer 100 and the controller 600 of the non-invasive biometric sensor 100 may be implemented as one semiconductor chip.

Figure 7:
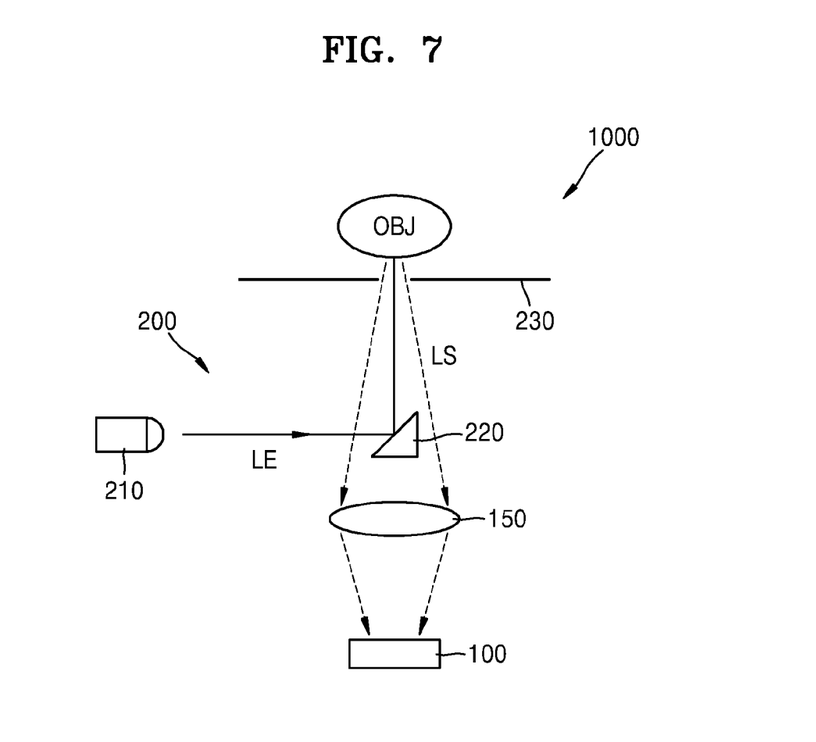
FIG. 7 illustrates an example of the optical arrangement of the non-invasive biometric sensor illustrated in FIG. 6.

FIG. 7 illustrates an example of the optical arrangement of the non-invasive biometric sensor 1000 illustrated in FIG. 6. Referring to FIG. 7, the non-invasive biometric sensor 1000 may be implemented as a reflection type. To this end, an optical system of the non-invasive biometric sensor 1000 may be configured such that the spectrometer 100 may sense the scattered light LS which is reflected from the object OBJ. For example, the light source unit 200 may include a light source 210, a light path converter 220, and a diaphragm 230. Although the light path converter 220 is illustrated as being a prism type, this is merely exemplary and the light path converter 220 may be a beam splitter type or a flat mirror type. The light path converter 220 may be omitted according to the position of the light source 210. Also, the light source unit 200 may further include an optical lens 150 configured to focus the scattered light LS from the object OBJ on the spectrometer 100.

The excitation light LE radiated from the light source 210 collides with a molecular structure in the object OBJ, is absorbed into the molecular structure, and is then emitted again, so that a wavelength-converted scattered light LS is output from the object OBJ. The scattered light LS, that is, a biometric optical signal may include various spectrums having different wavelength conversion degrees according to the molecular states in the object OBJ. The non-invasive biometric sensor 1000 according to the present exemplary embodiment includes an optical system structure in which the scattered light LS output along the same path as the input path of the excitation light LE to the object OBJ is input to the spectrometer 100. Also, according to an exemplary embodiment, the non-invasive biometric sensor 1000 may further include an additional optical device that branches the scattered light LS to the spectrometer 100.

Figure 8:
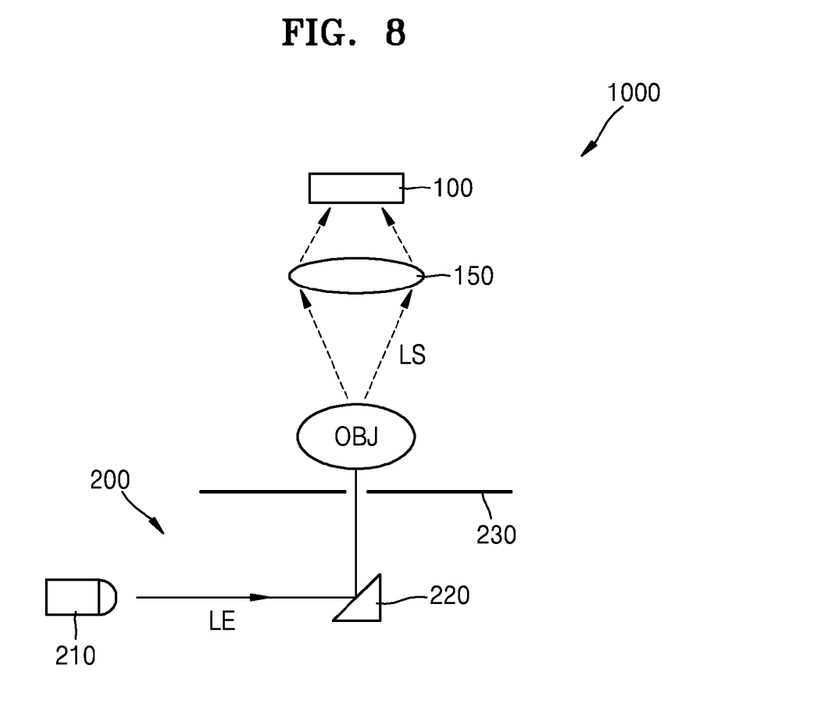
FIG. 8 illustrates another example of the optical arrangement of the non-invasive biometric sensor illustrated in FIG. 6.

FIG. 8 illustrates another example of the optical arrangement of the non-invasive biometric sensor 1000 illustrated in FIG. 6. Referring to FIG. 8, the non-invasive biometric sensor 1000 may be implemented as a transmission type. To this end, an optical system of the non-invasive biometric sensor 1000 may be configured such that the spectrometer 100 may sense the scattered light LS transmitted through the object OBJ. For example, the light source unit 200 may include a light source 210, a light path converter 220, and a diaphragm 230. Although the light path converter 220 is illustrated as being a prism type, this is merely exemplary and the light path converter 220 may be a beam splitter type or a flat mirror type. The light path converter 220 may be omitted according to the position of the light source 210. The light source unit 200 may further include an optical lens 150 configured to focus the scattered light LS from the object OBJ on the spectrometer 100.

The excitation light LE radiated from the light source 210 collides with a molecular structure in the object OBJ, is absorbed into the molecular structure, and is then emitted again, so that a wavelength-converted scattered light LS is output from the object OBJ. The scattered light LS, that is, a biometric optical signal may include various spectrums having different wavelength conversion degrees according to the molecular states in the object OBJ. The non-invasive biometric sensor 1000 according to the present exemplary embodiment includes an optical system structure in which the scattered light LS output through the object OBJ is input to the spectrometer 100.

Figure 9:
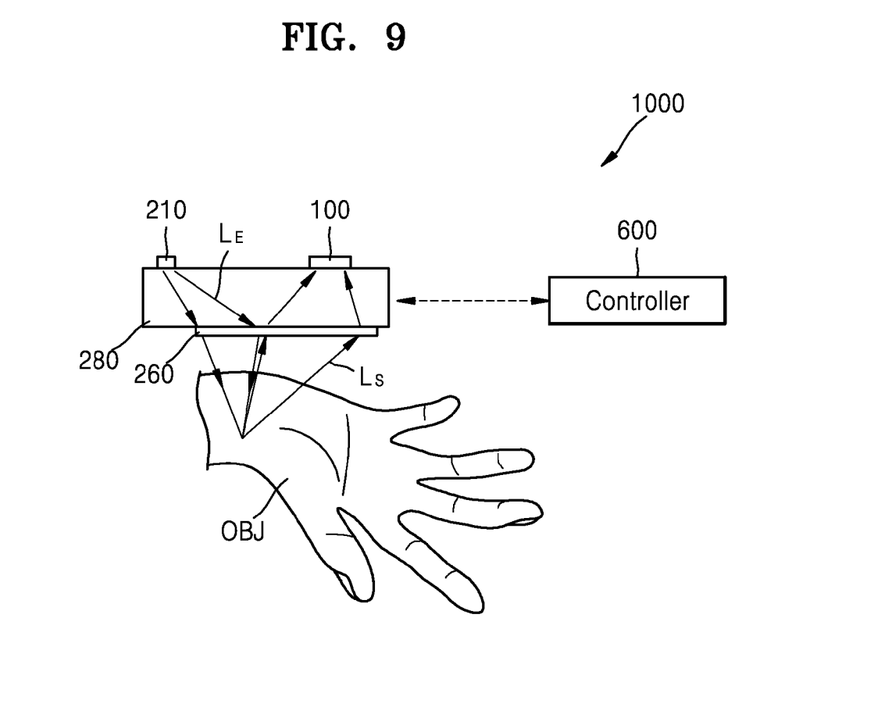
FIG. 9 illustrates another example of the optical arrangement of the non-invasive biometric sensor illustrated in FIG. 6.

FIG. 9 illustrates another example of the optical arrangement of the non-invasive biometric sensor 1000 illustrated in FIG. 6. Referring to FIG. 9, the non-invasive biometric sensor 1000 may further include a base 280, and the light source 210 and the spectrometer 100 may be disposed on the same surface of the base 280 or on different surfaces of the base 280. For example, the base 280 may be formed of a transparent material, and the light source 210 and the spectrometer 100 may be disposed on the same surface of the base 280 while being spaced apart from each other. In this case, the light source 210 may be disposed to radiate the excitation light LE to the object OBJ through the base 280. The spectrometer 100 may be disposed to sense the scattered light LS that is input from the object OBJ through the base 280. Also, on the other surface of the base 280, an optical lens 260 may be further disposed to focus the excitation light LE from the light source 210 on the object OBJ and focus the scattered light LS from the object OBJ on the spectrometer 100.

The base 280 may be formed of a flexible material. In this case, the non-invasive biometric sensor 1000 may be configured to be wearable on the object OBJ. For example, the non-invasive biometric sensor 1000 may be implemented as an armlet-type non-invasive blood sugar sensor. In this case, the controller 600 may be disposed on the base 280 together with the spectrometer 100. As another example, the non-invasive biometric sensor 1000 may be implemented in such a manner that only the light source 210 and the spectrometer 100 are formed in an armlet-type wearable structure and the controller 600 is mounted on a mobile device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A spectrometer comprising:
   a stacked light absorbing structure comprising a plurality of absorbing layers stacked in a vertical direction and having a plurality of absorption wavelength bands, and a plurality of tunnel junction layers respectively interposed between the plurality of absorbing layers to electrically connect the plurality of absorbing layers;
   a light source configured to generate an illumination light including the plurality of absorption wavelength bands of the plurality of absorbing layers;
   a notch filter array disposed between the light source and the stacked light absorbing structure and comprising a plurality of notch filters having a plurality of absorption characteristics to block only a wavelength band selected from among the plurality of absorption wavelength bands; and
   a controller configured to control the notch filter array to rotate according to a lapse of time to change, in a sequential order, the selected wavelength band to be blocked among the plurality of absorption wavelength bands.

2. The spectrometer of claim 1, wherein
   each of the plurality of notch filters has a sector shape, and
   the notch filter array has a rotatable disk shape that is formed by connecting the plurality of notch filters on a rotation axis.

3. The spectrometer of claim 1, wherein
   each of the plurality of absorbing layers comprises a positive-negative (p-n) junction, and
   each of the plurality of tunnel junction layers comprises a p-n junction that is doped at a higher doping concentration than the p-n junction of each of the plurality of absorbing layers.

4. The spectrometer of claim 1, wherein
   the plurality of absorbing layers are arranged in descending order of energy band gap from a light input side, and
   each of the plurality of tunnel junction layers has a larger energy band gap than the plurality of absorbing layers.

5. The spectrometer of claim 1, wherein the plurality of absorbing layers and the plurality of tunnel junction layers comprise a compound semiconductor.

6. The spectrometer of claim 5, wherein the plurality of absorbing layers and the plurality of tunnel junction layers are formed of a material comprising any one selected from a combination comprising gallium arsenic phosphide (GaAsP), gallium arsenide (GaAs), and indium gallium arsenide (InGaAs), a combination comprising aluminum gallium arsenide (AlGaAs), GaAs, and InGaAs, a combination comprising InGaAs, GaAs, and gallium phosphide (GaP), and a combination comprising indium arsenide (InAs), GaAs, and gallium nitride (GaN).

7. The spectrometer of claim 1, wherein
   each of the plurality of absorbing layers has a thickness of about 10 nm to about 10 μm, and
   each of the plurality of tunnel junction layers has a thickness of about 10 nm to about 100 nm.

8. The spectrometer of claim 1, further comprising:
   a first electrode disposed on a bottom surface of the stacked light absorbing structure; and
   a second electrode disposed on a top surface of the stacked light absorbing structure,
   wherein the plurality of absorbing layers are electrically connected in series between the first electrode and the second electrode.

9. The spectrometer of claim 8, wherein
   the first electrode is disposed on a bottom surface of an absorbing layer having the smallest energy band gap among the plurality of absorbing layers, and
   the second electrode is disposed on a top surface of an absorbing layer having the largest energy band gap among the plurality of absorbing layers.

10. The spectrometer of claim 1, wherein the controller is configured to obtain a photocurrent generated by the stacked light absorbing structure in response to the selected wavelength band to be blocked being changed.

11. The spectrometer of claim 10, wherein the controller is configured to store a pre-measured external quantum efficiency or short-circuit current density of each of the plurality of absorbing layers.

12. A non-invasive biometric sensor comprising:
   a spectrometer configured to obtain a spectrum distribution of a scattered light, which is generated from an object by an excitation light; and
   a controller configured to control operations of the spectrometer and analyze properties of the object by using signals provided by the spectrometer,
   the spectrometer comprising:
      a stacked light absorbing structure comprising a plurality of absorbing layers stacked in a vertical direction and having a plurality of absorption wavelength bands, and a plurality of tunnel junction layers respectively interposed between the plurality of absorbing layers to electrically connect the plurality of absorbing layers;
      a light source configured to generate an illumination light including the plurality of absorption wavelength bands of the plurality of absorbing layers; and
      a notch filter array disposed between the light source and the stacked light absorbing structure and comprising a plurality of notch filters having a plurality of absorption characteristics to block only a wavelength band selected from among the plurality of absorption wavelength bands,
   wherein the controller is configured to control the notch filter array to rotate according to a lapse of time to change, in a sequential order, the selected wavelength band to be blocked among the plurality of absorption wavelength bands.

13. The non-invasive biometric sensor of claim 12, wherein
the scattered light and the illumination light are together input to a light input surface of the stacked light absorbing structure, and
the notch filter array is disposed only on a path of the illumination light.

14. The non-invasive biometric sensor of claim 12, wherein the controller is configured to store a pre-measured external quantum efficiency or short-circuit current density of each of the plurality of absorbing layers.

15. The non-invasive biometric sensor of claim 14, wherein the controller is configured to obtain a photocurrent generated by the stacked light absorbing structure in response to the selected wavelength band to be blocked being changed.

16. The non-invasive biometric sensor of claim 15, wherein the controller is configured to calculate the spectrum distribution of the scattered light by using the pre-measured external quantum efficiency or short-circuit current density of each of the plurality of absorbing layers and photocurrent values of the stacked light absorbing structure that are obtained in response to the selected wavelength band to be blocked being changed.

17. The non-invasive biometric sensor of claim 12, further comprising a signal processor configured to analyze the properties of the object based on the spectrum distribution of the scattered light.

18. A non-invasive biometric sensing method comprising:
radiating an excitation light to an object;
providing a scattered light, which is generated from the object by the excitation light, to a stacked light absorbing structure, the stacked light absorbing structure comprising first to Nth absorbing layers stacked in a vertical direction and having different first to Nth absorption wavelength bands, and a plurality of tunnel junction layers respectively interposed between the first to Nth absorbing layers to electrically connect the first to Nth absorbing layers;
providing the stacked light absorbing structure with an illumination light for saturation of the second to Nth absorbing layers, other than the first absorbing layer, together with the providing of the scattered light, by using a notch filter array to block only the first absorption wavelength band selected from among the first to Nth absorption wavelength bands;
obtaining a first photocurrent generated by the stacked light absorbing structure;
calculating a light amount of a first wavelength band component in the scattered light by using the obtained first photocurrent; and
repeating a photocurrent obtaining operation to calculate light amounts of a second wavelength band component to an Nth wavelength band component in the scattered light, by controlling the notch filter array to rotate according to a lapse of time to change, in a sequential order, an absorption wavelength band to be blocked selected from among the first to Nth absorption wavelength bands.

19. The non-invasive biometric sensing method of claim 18, wherein the repeating comprises, after the calculating of the light amount of the first wavelength band component in the scattered light:
providing the stacked light absorbing structure with an illumination light for saturation of the first and third to Nth absorbing layers, other than a second absorbing layer, together with the providing of the scattered light;
obtaining a second photocurrent generated by the stacked light absorbing structure; and
calculating a light amount of the second wavelength band component in the scattered light by using the obtained second photocurrent.

20. The non-invasive biometric sensing method of claim 18, wherein the calculating of the light amount of the first wavelength band component in the scattered light by using the obtained first photocurrent comprises calculating the light amount of the first wavelength band component in the scattered light by comparing the obtained first photocurrent with a pre-measured short-circuit current density of the first absorbing layer.

21. A biological signal sensor comprising:
a stacked light absorbing structure comprising a plurality of light absorption layers configured to receive a light that saturates the plurality of light absorption layers excluding one of the plurality of light absorption layers and receive a bio-optical signal that activates the excluded light absorption layer, each of the plurality of light absorption layers being configured to absorb a different wavelength band of an optical spectrum;
a light source configured to generate an illumination light including a plurality of absorption wavelength bands of the plurality of light absorption layers;
a notch filter array disposed between the light source and the stacked light absorbing structure and comprising a plurality of notch filters having a plurality of absorption characteristics to block only a wavelength band selected from among the plurality of absorption wavelength bands; and
a controller configured to control the notch filter array to rotate according to a lapse of time to change, in a sequential order, the selected wavelength band to be blocked among the plurality of absorption wavelength bands, and obtain a photocurrent generated from the stacked light absorbing structure and analyze the bio-optical signal based on the obtained photocurrent.

22. The biological signal sensor of claim 21, further comprising a memory configured to store a pre-measured short-circuit current density of the excluded light absorption layer,
wherein the controller is further configured to compare the obtained photocurrent to the pre-measured short-circuit current density to analyze the bio-optical signal.

23. The biological signal sensor of claim 21, further comprising:
another light source configured to radiate a light towards a target subject to be reflected therefrom,
wherein the reflected light carries the bio-optical signal.

* * * * *